United States Patent [19]
Augello et al.

[11] Patent Number: 5,904,937
[45] Date of Patent: May 18, 1999

[54] TASTE MASKED PHARMACEUTICAL COMPOSITIONS

[75] Inventors: Michael Augello, Marlboro; Ronald S. Vladyka, Jr., Somerset, both of N.J.; Sheila M. Dell, New Hope, Pa.

[73] Assignee: FMC Corporation, Philadelphia, Pa.

[21] Appl. No.: 08/942,962

[22] Filed: Oct. 3, 1997

[51] Int. Cl.$^6$ ................................. A61K 9/20; A61K 9/28
[52] U.S. Cl. ........................ 424/494; 424/489; 424/441; 424/464; 424/465; 424/488
[58] Field of Search ...................... 424/464, 494, 424/488, 489, 441, 465

[56] References Cited

U.S. PATENT DOCUMENTS

| | | |
|---|---|---|
| 4,835,187 | 5/1989 | Reuter et al. . |
| 5,075,114 | 12/1991 | Roche . |
| 5,084,278 | 1/1992 | Mehta . |
| 5,137,730 | 8/1992 | Dennis et al. . |
| 5,215,755 | 6/1993 | Roche et al. . |
| 5,225,201 | 7/1993 | Beaurline . |
| 5,260,072 | 11/1993 | Roche et al. . |
| 5,489,436 | 2/1996 | Hoy et al. . |
| 5,529,783 | 6/1996 | Burke et al. . |
| 5,587,179 | 12/1996 | Gergely et al. . |
| 5,637,313 | 6/1997 | Chau et al. . |
| 5,639,475 | 6/1997 | Bettman et al. . |
| 5,653,993 | 8/1997 | Ghanta et al. . |
| 5,665,782 | 9/1997 | Alexander et al. . |
| 5,686,107 | 11/1997 | Ratnaraj et al. . |
| 5,747,068 | 5/1998 | Mendizabal . |

FOREIGN PATENT DOCUMENTS

WO 93/12768  7/1993  WIPO .

*Primary Examiner*—Thurman K. Page
*Assistant Examiner*—Brian K. Seidleck
*Attorney, Agent, or Firm*—Ratner & Prestia; Robert L. Andersen; Robert Silverman

[57] ABSTRACT

The present invention discloses the taste masking of drugs by wet granulating the drug with a microcrystaline cellulose compositions then spheronizing the granulation into spheres having a smooth uniform surface and a particle size in the range of 1 to 1000 microns.

11 Claims, No Drawings

TASTE MASKED PHARMACEUTICAL COMPOSITIONS

This invention relates to chewable pharmaceutical compositions in which the disagreeable taste of pharmaceutically active agent is masked by the physical form of the composition. More particularly it relates to a simple, economical and effective method for preparing taste masked compositions, to such compositions, and to chewable tablets made therefrom, in which the active agent is blended with a microcrystalline cellulose composition, wet granulated, and formed into taste masked spheres.

Ibuprofen is a widely used analgesic and antipyretic which is not palatable enough to be used in chewable tablets for those people who do not swallow whole solid-type dosage forms. Ibuprofen is quite bitter. Flavoring agents such as chocolate, anise, fruit flavors and the like have been proposed for use with and used with bitter tasting drugs. However, favoring agents are not reliable masking agents for ibuprofen as its bitter properties are very difficult to mask to any appreciable extent. The most successful methods for masking the taste of ibuprofen have typically involved coating ibuprofen particles with a barrier or coating that will not dissolve in the mouth but will readily dissolve in gastric fluids. However, many coatings which resist breaking during chewing also tend to retard bioavailability and/or release of the drug.

A therapeutic taste-neutral powder form of spray dried ibuprofen powder consisting essentially of 40% to 70% by weight ibuprofen, 15% to 50 % by weight of a cellulose material selected from ethylcellulose, hydroxyethylcellulose, hydroxypropylmethylcellulose and admixtures thereof and 5% to 40% by weight colloidal silica is known from U.S. Pat. No. 4,835,187.

The powder is obtained by spray drying a suspension of the colloidal silica in a lower alkanol solution of the ibuprofen and the cellulose material. The process involves mixing two separate slurries of ingredients, filtering them, then mixing the two filtrates and spray drying the combined slurry. A simpler more effective process for masking the bitter taste of ibuprofen is highly desirable.

U.S. Pat. No. 5,215,755 describes chewable tablets and taste masked granules for making the same, in which the granules were prepared by rotogranulation of the active with polyvinylpyrrolidone, sodium starch glycolate and sodium lauryl sulfate and coated with hydroxyethyl cellulose or a mixture of hydroxyethyl cellulose and hydroxypropylmethyl cellulose. This coating is said to achieve a beneficial balance of taste masking and bioavailability. Microcrystalline cellulose is disclosed as a binder for the granules in the compressed chewable tablets.

Microcrystalline cellulose, an excipient commonly used primarily as a binder in compressed pharmaceutical tablets, alone or in combination with other excipients, flavoring agents, sweetening agents or other common tablet adjuvants, was heretofore known or believed to be ineffective in masking the taste of ibuprofen or other similar bitter tasting active ingredients.

Surprisingly, it has now been found that microcrystalline cellulose excipient compositions readily mask the objectionable taste of ibuprofen and other like pharmaceutically active agents having an objectionable taste when small amounts of microcrystaline cellulose compositions are wet granulated with the agent then formed into substantially spherical particles having a substantially smooth, even surface and an average particle size of not more than about 1000 micrometers.

The microcrystalline cellulose compositions useful in the present invention are all well known to those skilled in the art and include microcrystalline cellulose per se, a product sold for example under the designation Avicel® PH-101 by FMC Corporation, Philadelphia, Pa. Suitable microcrystalline compositions also include blends of microcrystalline cellulose with various hydrocolloids, advantageously compatible hydrophilic colloids including methylcellulose, hydroxypropylmethylcellulose, hydroxypropylcellulose, hydroxy-ethylcellulose, carboxymethylcellulose sodium and gums such as guar gum, locust bean gum, konjac, xanthan, alginates, and combinations thereof. Suitably the weight ratio of microcrystalline cellulose to hydrocolloid, when they are used in combination, is in the range of about 80:20 to about 99:1, preferably 85:15 to 95:5. The preferred microcristaline cellulose compositions are coprocessed aggregates of microcrystalline cellulose and a hydrophilic hydrocolloid, preferably methylcellulose in which the weight ratio of microcrystalline cellulose to methylcellulose is from 99:1 to about 90:10, desirably 97.5:2.5 to about 92.5:7.5

The preferred coprocessed aggregate of microcrystalline cellulose and methylcellulose is disclosed in PCT Application WO93/12768 published Jul. 8, 1993 as a spheronizing agent useful for the production of more uniform spheres having high drug loading. The patent indicates the drug loaded spheres are useful as a substrate for coating and inclusion in controlled release and/or sustained release drug delivery systems.

The coprocessed aggregates of microcrystalline cellulose and methylcellulose are prepared in a known manner, as more fully described in the above identified PCT application, which is hereby incorporated herein by reference. In general, microcrystalline cellulose or an aqueous dispersion thereof is combined with an aqueous solution of hydrocolloid under high energy shear until the mixture has reached equilibrium. After blending is complete, the slurry is dried, preferably by spray drying, to produce a dried coprocessed aggregate of microcrystalline cellulose and hydrocolloid that has significantly different properties from either of the separate components or of a simple blend of the two components. The microcrystalline cellulose/ methylcellulose aggregate is available for example as Avicel®, Sphere Grade from FMC Corporation, Philadelphia, Pa., as an aggregate containing 95% microcrystalline cellulose, 5% methylcellulose.

In accordance with the present invention, taste masked pharmaceutical compositions are advantageously obtained by (a) blending together 70 to 90 parts by weight of a pharmaceutically active agent which is water insoluble or only slightly soluble and has an objectionable taste; and from 10 to 30 parts by weight of a microcrystalline cellulose excipient composition, to form a dry blend of said agent and said excipient; (b) adding to the resulting blend, with agitation or stirring, from about 35 to 65 parts by weight of water for each 100 parts by weight of blend to form a wet granulation in which the water is evenly distributed throughout, then (c) forming granular, taste masked, substantially spherical particles having a smooth uniform surface and a particle size of up to 1000 micrometers, suitably in the range of about 100 to about 1000 micrometers, preferably about 250 to about 900 micrometers.

While the best mode for practicing the invention contemplates the use of extrusion spheronization in step (c), it is also highly effective to form the smooth sphere shaped particles using techniques such as a high shear granulation or rotogranulation and the like, as indicated below.

Extrusion spheronization involves the steps of dry blending drug and excipients; wet granulation of the dry blend; extrusion of the wet granulation mass through a screen having openings of about 0.5 to about 2.5 mm preferably about 0.6 to 2.0, and most preferably about 0.8 to about 1.5 mm to produce compacted cylindrical spaghetti-like or ribbon-like strands; and spheronizing the strands in a spheronizer. The latter is essentially a device equipped with a grooved or serrated rotating disk. Under the tumbling/roping-like action of the rotating disk, the cylindrical strands are broken into smaller segments which undergo smoothing and rounding to form the spheroids which are then dried. For a more detailed description of the spheronization process, reference is made to "A New Technique for the Production of Spherical Particles" by A.D. Reynolds in Manufacturing Chemist, Aerosol News, V41, (Jun), p 40–43, 1970.

In accordance with the extrusion spheronization embodiment, taste-neutral compositions are prepared by extrusion spheronization of a composition containing, for example about 70 to about 90 parts by weight of active agent, about 10 to about 30, preferably about 10 to about 15, parts by weight of a dried coprocessed aggregate of microcrystalline cellulose and methylcellulose or other microcrystalline composition or blend, and optionally about 4 to about 8, preferably about 4.5 to about 7 parts by weight of dicalcium phosphate. The active agent and microcrystalline cellulose composition particles are first dry blended until thoroughly mixed into a dry blend. To the dry blend is added about 35 to about 65 parts by weight of water per 100 parts of dry blend, with mixing until an extrudable granular product is obtained. The granular product is then extruded through a screen preferably having openings of about 0.8 mm to about 1.5 mm. The extrudate is then placed in a spheronizer for a period of time sufficient to form spheres having smooth, uniform surface and preferably spheres having an average particle size diameter in the range of about 300 to about 800 micrometers. The spheres are then dried at elevated temperature to a moisture content of less than 5%, preferably 3–5%, by any conventional drying means.

In accordance with a granulation embodiment, about 70 to about 85 parts by weight of pharmaceutically active agent and about 15 to about 30 parts by weight of microcrystalline cellulose composition, blend, or aggregate a blended in a high shear granulator until mixing is complete, then about 35 to about 50 parts by weight of water per 100 parts by weight of dry blend is fed to the granulator by gravity feed through a spray nozzle, increasing the blade speed and continuing granulation until the resulting spheres have a smooth uniform surface, and preferably a mean particle size in the range of about 250 to about 900 micrometers. The resulting spheres may then be dried at an elevated temperature or by other suitable means.

The present invention is particularly advantageous for producing taste neutral spherical compositions having extremely high drug loading, for example in the range of 70% to about 90% by weight of the resulting compositions. Thus, the composition aspect of this invention provides taste-neutral spherical particulate compositions having a mean particle size in the range of 300 to 800 microns comprising from about 70 to about 90 parts by weight pharmaceutically active ingredient, from about 10 to 30 parts by weight of microcrystalline cellulose composition, and optionally from 4 to 7 parts by weight of an alkaline earth metal phosphate, preferably a calcium phosphate such as dicalcium phosphate.

One skilled in this art will appreciate that numerous pharmaceutically active agents which may need to be chewed rather than swallowed as a compressed tablet, but have a taste which is objectionable to patients, may be taste masked in accordance with the method of this invention. In addition to having an objectionable taste, the active agents prepared according to this invention should also be sufficiently water insoluble to permit a slightly extended time in the mouth while being chewed and before being swallowed. One skilled in the art will also appreciate that in certain drugs the pH of the composition may need to be adjusted in order to attain the desired degree of taste masking. One skilled in the art will also appreciate that the present invention contemplates and includes the addition of other adjuvants normally used in the preparation of chewable tablets, including binders, sweeteners, flavors and disintegrants, may be employed in tableting the spheres of this invention into chewable tablets.

Accordingly the invention contemplates the use of the present invention for preparation of spheres and chewable tablets containing such active ingredients as:

ibuprofen, ketoprofen, carprofen, fenoprofen calcium, naproxen and/or combinations thereof, either alone or in combination with other pharmaceutically active ingredients.

The following examples illustrate the present invention with examples of preparation of chewable ibuprofen and ketoprofen compositions of the invention and tablets made therefrom in which the unpleasant flavor of the active is reduced essentially completely, making the tablets palatable and, therefore, acceptable to consumers, while having virtually no adverse impact on bioavailability of the drug in question.

EXAMPLE 1

Granulation and Spheronization of Ibuprofen

In the bowl of a Hobart mixer were placed 1700 grams of ibuprofen (Albemarle Corp.), 200 grams of Avicel® (Sphere Grade, FMC Corporation), and 100 grams of dicalcium phosphate. To this dry mixture was added, with stirring, 800 grams of deionized water. The granulation was then extruded through a screen having openings of 0.8 mm. The extrudate was placed in a spheronizer operated at 800 rpm for 15 minutes. The resulting spheres were then dried in an oven at 50° C. for 12 hours. When these spheres were tasted, the unpleasant taste of ibuprofen had been reduced by about 75–80% making the finished spheres acceptable and palatable.

The spheres were fractionated into two fractions of particle sizes. The first fraction passed through a Number 20 US Standard Sieve and not through a Number 30 US Standard Sieve, (590–840 microns), and the second fraction passes through a Number 35 Standard sieve and not through a Number 50 Standard Sieve (297–500 microns).

EXAMPLE 2

Ibuprofen Chewable Tablets

The second fraction produced in Example 1 (336.4 grams) and 357.2 grams of glyceryl monostearate (Myvaplex® 600, Eastman Chemical Co.) were placed in a twin shell blender and mixed for 10 minutes. At the conclusion of this time, 285.8 grams of Pregelatinized Starch (Starch 1500, Colorcon), 857.4 grams of mannitol, 14.2 grams of aspartame (The NutraSweet Co.), 20 grams of citric acid, 20 grams of Avicel® CE (FMC Corporation), 20 grams of ProSweet, 57.02 grams of Golden Punch durarome #730104

(Firminich, Inc.), and 14.2 grams of punch berry 65863317P Firminich, Inc.) were added to the contents of the twin shell blender, and mixing was continued for 15 additional minutes. Finally, 20 grams of magnesium stearate was added to the mixture with 5 minutes more mixing. Prior to adding each material to the blender, it was passed through a Number 30 US Standard sieve (ASTM E 11). This mixture was then compressed into a tablet. The taste of the ibuprofen was essentially undetectable when promptly chewed and ingested.

EXAMPLE 3

Wet Granulation of Ibuprofen

In a high shear granulator were placed 2250 grams of ibuprofen (Albemarle Corp.) and 750 grams of Avicel® (Sphere Grade, FMC Corporation). The blade was operated at 300 rpm for three (3) minutes to mix the components, and the cross screw was operated at 1800 rpm. After this mixing was complete, 1147.5 grams of deionized water was fed into the granulator by gravity through a spray nozzle. When the water had been completely added, the bowl was scraped, and then the speed of the blade was increased to 600 rpm. Seven (7) minutes later the bowl was again scraped. The total time for this granulation was 44 minutes. The resulting spheres were then dried in an oven at 50° C. for twelve (12) hours. The particles made by this process were somewhat round with particle sizes ranging from less then 840 microns (20 mesh) to more than 250 microns (60 mesh). When these granules were tasted, the unpleasant taste of ibuprofen was greatly reduced.

EXAMPLE 4

Chewable Tablets Prepared from Wet Granulated Ibuprofen

In a twin shell blender were placed 369.6 grams of the dried wet granulation of Example 3, 369.6 grams glyceryl monostearate (Myvaplex® 600, Eastman Chemical Co.), 33.2 grams of aspartame (The NutraSweet Co.), 21.6 grams of apple cinnamon durarome #860.310/TD 05.91 (Firminich Inc.), and 27.6 grams of an artificial special compound flavor (Firminish Inc.). This mixture was blended for 10 minutes after which 138.6 grams of Pregelatinized Starch (Starch 1500 Colorcon), 969.8 grams of granular mannitol, and 27.6 grams of crosslinked sodium carboxymethylcellulose (Accelerate™, FMC Corporation) were added to the blender. Mixing was continued for 10 more minutes, and then 19.4 grams of magnesium stearate was added to the blender. Mixing was completed in five minutes. Prior to adding each material to the blender, it was passed through a Number 30 US Standard Sieve. This mixture was then compressed into a tablet. The particle size distribution of the granulation used in this formulation was determined by using a Sonic Sifter, a vibrated stack of U.S. Standard Sieves in which each succeeding sieve is finer in mesh than the one above it. The amount of product retained on each sieve provides the percentage of particles larger than that sieve, but smaller then the next higher sieve. Particles having sizes in each mesh range were: 48.23%>297 microns (>50 mesh); 29.657% 177–297 microns (50–80 mesh); 5.39% 149–177 microns (80–100 mesh); 13.57% 74–149 microns (100–200 mesh); 3.17% 53–74 microns (200–270 mesh); and 5.00%<53 microns (<270 mesh). The loose bulk density of this material was 0.6164 grams/mL. The water content of the granulation was 1.50%. Properties of the chewable tablets include tablet thickness (3.25 mm, 0.1279 inch), hardness (5.37 kiloponds), and disintegration time in 37° C. purified water (184 seconds). All of these measurements were taken on ten tablets except disintegration time which used six tablets. The unpleasant flavor of ibuprofen was effectively masked by using the wet granulation in combination with other excipients.

EXAMPLE 5

Granulation and spheronization of ketoprofen

In the bowl of a Powerex granulator were placed 2400 grams of ketoprofen, 420 grams of Avicel® (Sphere Grade, FMC Corporation), 75 grams of Methocel® A15LV (Dow Chemical Co.), 60 grams of dibasic sodium phosphate, and 15 grams of sodium lauryl sulfate. This dry mixture was blended for 5 minutes. A solution of 15 grams of Polysorbate 80 was prepared in 100 mL of deionized water which was then mixed with 1100 mL of deionized water The granulator was operated at a blade speed of 150 rpm and the cross screw at 1800 rpm. The aqueous solution was pumped to the granulator at 75 mL/minute The granulation was then extruded through a screen having 1 mm openings. The extrudate was placed in a spheronizer operated at 800 rpm for 15 minutes. The resulting spheres were then dried in an oven at 65° C. for 1 hour. When these spheres were tasted, the unpleasant taste of ketoprofen had been reduced by about 75–80%, making the finished spheres acceptable and palatable.

EXAMPLE 6

Ketoprofen chewable tablets

The spheres produced in Example 5 (92.6 grams) and 296.2 grams of concentrated glyceryl monostearate (Myvaplex® 600, Eastman Chemical Co.) were placed in a twin shell blender and mixed for 10 minutes. At the conclusion of this time, 148 grams of Starch 1500 (Colorcon), 888.6 grams of mannitol, 42 grams of aspartame (The NutraSweet Co.), 296.2 grams of Avicel® PH-102 (FMC Corporation), 12 grams of Firmenich Special Compound (a flavoring agent), 71 grams of Tutti Fruiti Flavor, 29.6 grams of croscarmellose sodium (Ac-Di-Sol®, FMC Corporation), 100 grams of Avicel® CE-15 were added to the contents of the twin shell blender, and mixing was continued for 15 additional minutes. Finally, 24 grams of magnesium stearate was added to the mixture with 5 minutes more mixing. Prior to adding each material to the blender, it was passed through a 30 mesh US standard sieve. This mixture was then compressed using a Stokes B-2 tablet press fitted with 11.1 mm (0.438 inch) round, flat faced tooling. An upper compression force of 1063.12 Kg and a lower compression force of 982 Kg were used. The tablets produced had an average weight of 0.3376 grams and thickness of 4.27 mm (0.1682 inch). The taste of the ketoprofen was essentially masked because of the effectiveness of the spheronized formulation combined with the other excipients that were included in the final tablet formulation.

EXAMPLE 7

Granulation and spheronization of ibuprofen using methylcellulose and microcrystalline cellulose In a Hobart mixing bowl 750 grams of ibuprofen, 12.5 grams of Methocel® A15LV (Dow Chemical Co.), and 237.5 grams off microcrystalline cellulose (Avicel® PH-101, FMC Corporation) were dry blended for 5 minutes.

Water (450 grains) was then added to the contents of the bowl while continuing mixing for a period of at least 15 minutes. The wet granulation produced in this manner was then extruded through a screen having openings of 0.8 at a feed speed of 50 rpm and an agitator speed of 25 rpm. The exudate was placed in a spheronizer for 2 to 5 minutes at a speed of 500 rpm with minimal purge air pressure. The collected spheres were dried in a 50° C. oven for 12 hours. When these spheres were tasted, the tastemasking was comparable to that produced in Example 1.

EXAMPLE 8

Granulation and spheronization of ibuprofen using microcrystalline cellulose

In a Hobart mixing bowl 750 grams of ibuprofen, and 250 grams of microcrystalline cellulose (Avicel® PH-101, FMC Corporation) were dry blended for 5 minutes. Water (600 grams) was then added to the contents of the bowl while continuing mixing for a period of at least 15 minutes. The wet granulation produced in this manner was then extruded through a screen having openings measuring 0.8 mm at a feed speed of 50 rpm and an agitator speed of 25 rpm. The exudate was placed in a spheronizer for 2 to 5 minutes at a speed of 500 rpm with minimal purge air pressure. The collected spheres were dried in a 50° C. oven for 12 hours. When these spheres were tasted, the tastemasking was comparable to that produced in Example 1.

We claim:

1. A method for preparing a taste masked pharmaceutical composition for compression into chewable pharmaceutical tablets which comprises:
    (a) blending together 70 to 90 parts by weight of a pharmaceutically active agent which is water insoluble or only slightly soluble and has an objectionable taste with from 10 to 30 parts by weight of a taste masking agent selected from the group consisting essentially of microcrystalline cellulose, microcrystalline cellulose coprocessed with methylcellulose, and a blend of microcrystalline cellulose and methylcellulose to form a dry blend of said active agent and said taste masking agent;
    (b) adding to the blend, with agitation or stirring, 35 to 65 parts by weight of water for each 100 parts by weight of dry blend to form a wet granulation in which the water is evenly distributed throughout;
    (c) then forming the wet granulation into taste-masked, spherical particles having a smooth uniform surface and a particle size in the range of 100 to 1000 micrometers.

2. The process of claim 1 in which the wet granulation is extruded through a screen having openings of 0.5 to 2.5 and spheronized in a spheronizer to form taste-masked spheres.

3. The process of claim 1 in which the wet granulation is prepared and formed into spheres utilizing a high shear granulator to form taste-masked spheres.

4. The process of claim 1 in which the taste masking agent is selected from the group consisting of (a) microcrystalline cellulose, (b) microcrystalline cellulose and methylcellulose in which the weight ratio of microcrystalline cellulose to methylcellulose is in the range of 99:1 to 90:10, and (c) a dried coprocessed aggregate of microcrystalline cellulose and methylcellulose in which the weight ratio of microcrystalline cellulose to methylcellulose is from 99:1 to about 90:10.

5. Taste-masked pharmaceutical compositions prepared by the process of claim 1, 2, 3, or 4 comprising from 70% to 90% by weight of the pharmaceutically active agent ibuprofen or ketoprofen.

6. Taste-masked chewable tablets comprising a pharmaceutically effective amount of the composition of claim 6 in admixture with pharmaceutically acceptable excipients and adjuvants.

7. Taste masked chewable tablets of claim 6 in which the pharmaceutically active agent is ibuprofen.

8. Taste masked chewable tablets of claim 7 in which the pharmaceutically active agent is ketoprofen.

9. A taste masked pharmaceutical composition consisting essentially of from 70 to 90 parts by weight of a pharmaceutically active agent which is water insoluble or only slightly soluble and has an objectionable taste and from 10 to 30 parts by weight of a taste masking agent selected from the group consisting of microcrystalline cellulose, microcrystalline cellulose coprocessed with methylcellulose, and a blend of microcrystalline cellulose and methylcellulose, said composition being in the form of spherical particles having a smooth uniform surface and a particle size in the range of 100 to 1000 micrometers.

10. The composition of claim 9 in which the taste masking agent is selected from the group consisting of (a) microcrystalline cellulose, (b) microcrystalline cellulose and methylcellulose in which the weight ratio of microcrystalline cellulose to methylcellulose is in the range of 99:1 to 90:10, and (c) a dried coprocessed aggregate of microcrystalline cellulose and methylcellulose in which the weight ratio of microcrystalline cellulose to methylcellulose is from 99:1 to about 90:10.

11. The taste-masked pharmaceutical compositions of claim 9 or 10, comprising from 70% to 90% by weight of the pharmaceutically active agent ibuprofen or ketoprofen.

* * * * *